United States Patent
Okinishi

(10) Patent No.: US 6,411,839 B1
(45) Date of Patent: Jun. 25, 2002

(54) FUNDUS BLOOD VESSEL EXAMINATION APPARATUS

(75) Inventor: Satoru Okinishi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/472,990

(22) Filed: Dec. 28, 1999

(30) Foreign Application Priority Data

Dec. 30, 1998 (JP) .......................................... 10-377636

(51) Int. Cl.⁷ ................................................ A61B 5/02
(52) U.S. Cl. ....................... 600/479; 600/476; 600/504; 351/211; 351/208
(58) Field of Search ................................ 600/479, 504

(56) References Cited

U.S. PATENT DOCUMENTS

| | | | |
|---|---|---|---|
| 5,106,184 A | * | 4/1992 | Milbocker |
| 5,129,400 A | * | 7/1992 | Makino et al. |
| 5,446,509 A | | 8/1995 | Okinishi ................. 351/206 |
| 5,830,147 A | * | 11/1998 | Feke et al. |
| 5,894,337 A | | 4/1999 | Okinishi et al. ............ 351/205 |
| 5,976,096 A | * | 11/1999 | Shimizu et al. |
| 6,192,269 B1 | * | 2/2001 | Okumura et al. |

FOREIGN PATENT DOCUMENTS

| JP | 9-145819 | 6/1997 |
|---|---|---|
| JP | 9-154819 | 6/1997 |

* cited by examiner

Primary Examiner—Marvin M. Lateef
Assistant Examiner—Runa Shah Qaderi
(74) Attorney, Agent, or Firm—Fitzpatrick, Cella, Harper & Scinto

(57) ABSTRACT

A blood vessel examination apparatus includes a presentation device for presenting a fixation reference mark to the eye to be examined, an irradiation device for irradiating a blood vessel on the fundus of an eye with measurement light in accordance with the position of the fixation reference mark, and a light-receiving device for receiving light of the measurement light reflected by the fundus The apparatus also includes a computation device for computing blood vessel information of a fundus blood vessel on the basis of a light-received output of the light-receiving device, a direction detector for detecting the longitudinal direction of the blood vessel, and a controller for controlling the position of the fixation reference mark in accordance with the direction detected by the direction detector, and obtaining accurate blood vessel information (e.g., blood flow velocity) by moving the measurement light along the blood vessel.

17 Claims, 6 Drawing Sheets

FUNDUS BLOOD VESSEL EXAMINATION APPARATUS

BACKGROUND OF THE INVENTION

1. Field of the Invention

The present invention relates to a fundus blood vessel examination apparatus used in equipment for measuring blood vessels of the fundus of an eye and blood flow or bloodstream information.

2. Related Background Art

Conventionally, a fundus hemodromometer or blood flow meter that can easily measure the absolute value of blood flow velocity on blood vessels of the fundus or eyeground of an eye using a Doppler shift is disclosed in Japanese Patent Application Laid-Open No. 9-154819. Such a fundus hemodromometer can reliably measure the blood flow velocity independently of the measurement portions of the blood vessels of the fundus. However, measurement is often disabled since a high-quality Doppler shift measurement signal cannot be obtained, depending on measurement positions even on a single blood vessel. This is because the blood vessels of the fundus are located deep inside a living body and indefinite factors of a living body have a large influence on such measurement.

However, in such case, by shifting the measurement position on a given blood vessel, a portion where a high-quality Doppler shift measurement signal can be obtained is detected. For this reason, a simple method of changing the measurement position on a blood vessel is required. As such method, a method in which an ophthalmic technician appropriately moves a fixation reference mark to change the direction of an eye to be examined of a patient, a method of deflecting a measurement light beam using a mirror, and the like, may be used.

However, in the above prior art, it is technically very difficult for the ophthalmic technician to change the measurement position by accurately tracking a blood vessel of the fundus that runs in a complicated pattern by his or her own sight and skills, and such technique is largely influenced by unstable fixation of an eye when a patient suffers a disease or is aged.

SUMMARY OF THE INVENTION

It is an object of the present invention to provide a fundus blood vessel examination apparatus, which can solve the aforementioned problems, and can move measurement light along the running direction of a blood vessel by automatically detecting the direction it runs.

It is another object of the present invention to provide a fundus blood vessel examination apparatus, which can accurately track measurement light on a blood vessel by a simple operation in combination with tracking of the diameter direction of the blood vessel.

It is still another object of the present invention to provide a fundus blood vessel examination apparatus, which evaluates the reliability of measurement data, and searches for a portion where optimal data can be obtained by automatically tracking measurement light on a blood vessel.

A fundus blood vessel examination apparatus according to the present invention comprises an irradiation optical system for irradiating a fundus blood vessel with measurement light, light-receiving means for receiving scattered light of the measurement light from the fundus blood vessel, measurement means for detecting predetermined information from the fundus blood vessel on the basis of information from the light-receiving means, direction detection means for detecting a direction in which a bloodstream flows in the fundus blood vessel, and control means for controlling the irradiation position on a fundus on the basis of the running direction information detected by the direction detection means, wherein the irradiation position moves along the direction in which the fundus blood vessel runs.

After the irradiation position of the measurement light is moved, the direction in which the fundus blood vessel runs is detected to determine a moving direction of the blood.

The measurement means comprises evaluation means for evaluating the reliability of the predetermined information, and the evaluation means evaluates the reliability of the predetermined information as needed after the irradiation position of the measurement light is moved.

The control means changes the irradiation position on the basis of an evaluation result of the evaluation means, and moves the measurement light to a nearby position where the predetermined information produces a predetermined reliability.

A fundus blood vessel measurement apparatus according to the present invention comprises:
  presentation means for presenting a fixation reference mark to an eye to be examined;
  irradiation means for irradiating a blood vessel on a fundus of an eye with measurement light in accordance with a position of the fixation reference mark;
  light-receiving means for receiving reflected light of the measurement light by the fundus;
  computation means for computing blood vessel information of a fundus blood vessel on the basis of a light-received output of the light-receiving means;
  direction detection means for detecting a longitudinal direction of the blood vessel; and
  position control means for controlling the position of the fixation reference mark in accordance with the direction detected by the direction detection means.

The apparatus further comprises an input member for changing the position of the fixation reference mark, and the position control means controls the position of the fixation reference mark on the basis of a direction detection signal from the direction detection means and an input signal of the input member.

The direction detection means comprises an image sensing element for sensing a blood vessel image.

The direction detection means further comprises an image rotator, which is inserted between the image sensing element and the eye to be examined, and is adapted to rotate the blood vessel image with respect to the image sensing element.

The image rotator is rotated in accordance with an output from the image sensing element.

The image rotator is rotated in accordance with an output from the image sensing element to locate the blood vessel image in a predetermined direction.

The direction detected by the direction detection means is a rotation angle of the image rotator.

The position control means controls the position of the fixation reference mark to irradiate the blood vessel with the measurement light along a longitudinal direction thereof.

The image sensing element comprises an array-type sensor.

Other features of the present invention will become apparent from the following description.

DETAILED DESCRIPTION OF THE PREFERRED EMBODIMENTS

The present invention will be described in detail hereinafter based on the illustrated embodiment.

Figure 1:
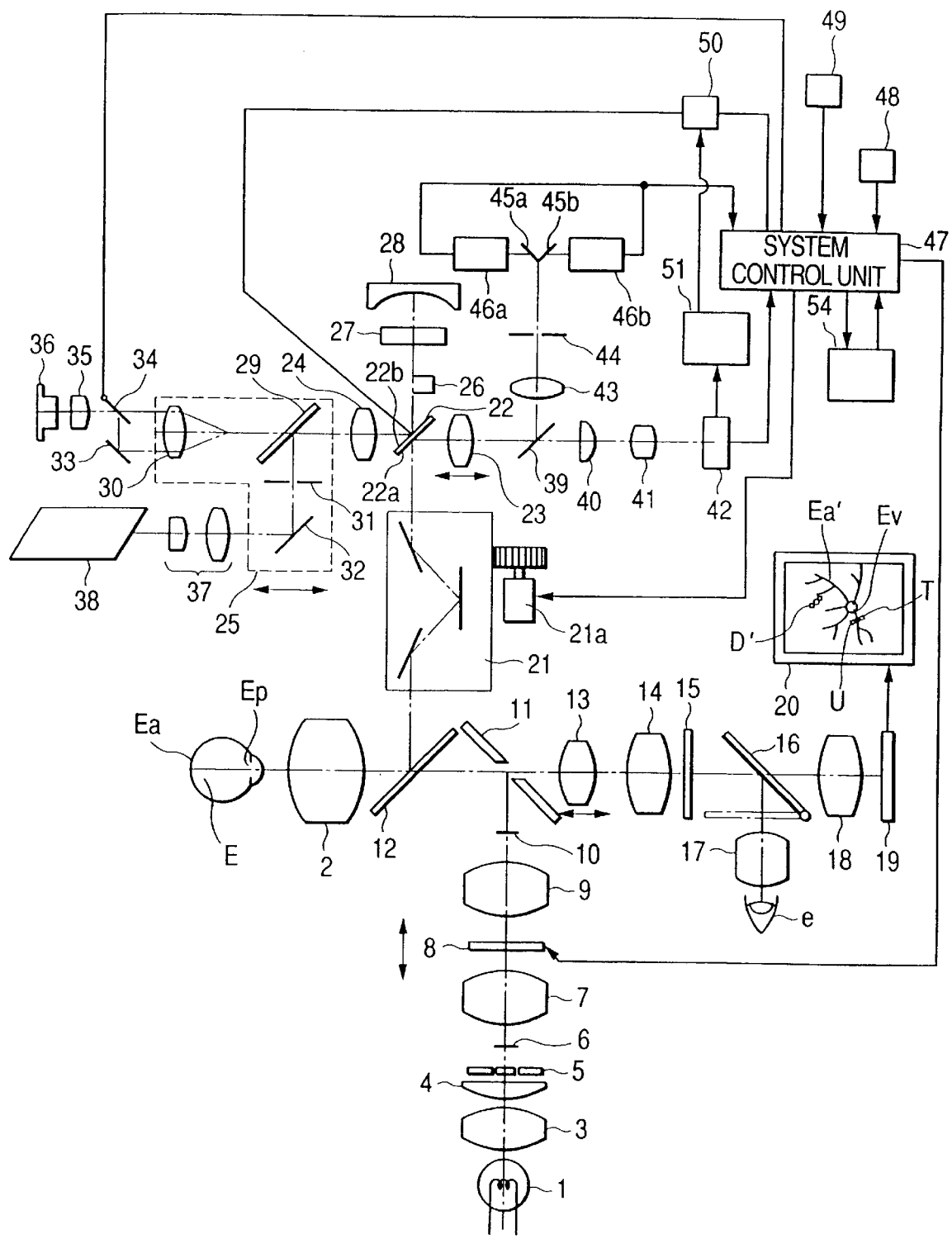
FIG. 1 is a view showing the structure of a fundus hemodromometer according to an embodiment of the present invention.

FIG. 1 shows the arrangement of a fundus blood vessel examination apparatus of this embodiment. On a fundus illumination optical path extending from an observation light source 1 e.g., a tungsten lamp for emitting white light to an objective lens 2 that opposes an eye E to be examined, a condenser lens 3, a field lens 4 with a bandpass filter that transmits only wavelength light in, e.g., the yellow wavelength range, a ring slit 5, which is set at a position nearly conjugate with a pupil Ep of the eye E to be examined, a light-shielding member 6, which is set at a position nearly conjugate with a lens of the eye E to be examined, a relay lens 7, a transmission liquid crystal plate 8, which is movable along the optical path and comprises a matrix of fine fixation-reference-mark-indication elements (FIG. 2), a relay lens 9, a light-shielding member 10, which is conjugate with a position near the cornea of the eye E to be examined, a mirror 11 with a hole, and a bandpass mirror 12, which transmits wavelength light in the yellow wavelength range and reflects most of other light beams, are inserted in turn. Note that the ring slit 5 and the light-shielding members 6 and 10 are used to split light into fundus illumination light and fundus observation light at a position in front of the eye E to be examined, and their shapes are not particularly limited as long as they can form a required light-shielding region.

A fundus observation optical system is built behind the mirror 11 with a hole, and a movable focusing lens 13, a relay lens 14. a scale plate 15, an optical path switching mirror 16, which is free to be inserted/removed into/from the optical path, and an eyepiece 17, are laid out in turn along the optical path that leads to an eye e of an ophthalmic technician. On the optical path when the optical path switching mirror 15 is located at the dotted line position in FIG. 1, a TV relay lens 18 and CCD camera 19 are arranged, and the output from the CCD camera 19 is connected to a liquid crystal monitor 20.

On the optical path in the reflecting direction of the bandpass mirror 12, an image rotator 21 which can be rotated by a driving means 21a, such as a motor or the like, and a galvanometric mirror 22, are arranged. The galvanometric mirror 22 rotates in a direction perpendicular to the plane of paper of FIG. 1, and has a notch portion and two polished surfaces. A focusing lens 23, which is movable along the optical path, is placed in the reflecting direction of a lower reflection surface 22a of the mirror 22, and a lens 24 and a focus unit 25, which is movable along the optical path, are arranged in the reflecting direction of an upper reflection surface 22b thereof. Note that the front focal plane of the lens 24 is conjugate with the pupil Ep of the eye E to be examined, and the galvanometric mirror 22 is located on this focal plane.

Behind the galvanometric mirror 22, an optical path length compensation meniscus plate 26, a sunspot plate 27 having a light-shielding portion in the optical path, and a concave mirror 28 are concentrically set on the optical path to provide the function of a relay optical system that forms −1× images of the upper and lower reflection mirrors 22b and 22a of the galvanometric mirror 22 in cooperation with each other. With this function, a light beam that passes without being reflected by the lower reflection surface 22a of the galvanometric mirror 22 is guided to the upper reflection surface 22b of the galvanometric mirror 22. Note that the optical path length compensation meniscus plate 26 is used to correct deviations of the positions of the upper and lower reflection surfaces 22b and 22a of the galvanometric mirror 22 in the up-and-down direction on the plane of the paper due to their mirror thickness, and has an effect in only the optical path extending toward the image rotator 21.

In the focus unit 25, a dichroic mirror 29 and condenser lens 30 are disposed on the same optical path as the lens 24, and a mask 31 and mirror 32 are disposed on the optical path in the reflecting direction of the dichroic mirror 29. The focus unit 25 is integrally movable in a direction indicated by the arrow. On the optical path in the incidence direction of the condenser lens 30, a stationary mirror 33 and an optical path switching mirror 34, which is retractable from the optical path, are inserted in parallel. Also, on the optical path in the incidence direction of the optical path switching mirror 34, a collimator lens 35 and a blood flow velocity measurement light source 36 comprising, e.g., a laser diode that emits coherent red light, are inserted. Furthermore, on the optical path in the incidence direction of the mirror 32, a beam expander 37, which comprises a cylindrical lens and the like, and a tracking light source 38 that emits, e.g., high-luminance green light, which is different from the light emitted by the measurement light source 36, are inserted. Note that tracking light emitted by this tracking light source 38 is also used in blood vessel shape measurement.

On the optical path in the reflecting direction of the lower reflection surface 22a of the galvanometric mirror 22, a dichroic mirror 39, a field lens 40, an enlargement lens 41, and a linear CCD 42 with an image intensifier, light-receiving elements of which are lined up in the longitudinal direction of tracking light, are set in turn behind the focusing lens 23 to construct a blood vessel detection system. Also on the optical path in the reflecting direction of the dichroic mirror 39, an imaging lens 43, a confocal stop 44, and a pair of mirrors 45a and 45b, which are nearly conjugate with the pupil Ep of the eye E to be examined, are disposed. In the reflecting directions of the mirrors 45a and 45b, photomultipliers 46a and 46b are respectively arranged to construct a measurement light-receiving optical system. Note that all the optical paths are illustrated on an identical plane for the sake of illustrative convenience. However, the reflecting optical paths of the mirrors 45a and 45b, the measurement optical path in the output direction of the tracking light source 38, and the optical path extending from the laser diode 36 to the mask 31 are perpendicular to the plane of the paper on which the figure is drawn.

Figure 3:
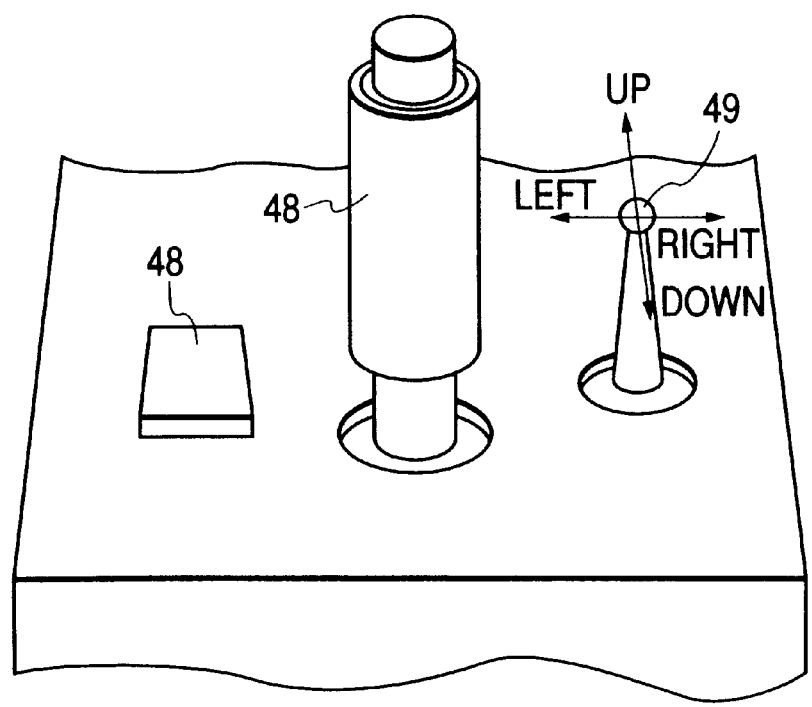
FIG. 3 is a perspective view of an operation input means.

A system control unit 47 controls the entire apparatus. The outputs of the photomultipliers 46a and 46b, the linear CCD 42, an operation input means 48 (FIG. 3) operated by the ophthalmic technician, and an input means 49 for moving the fixation reference mark are connected to the system control unit 47. The output of the system control unit 47 is connected to the transmission liquid crystal plate 8 and optical path switching mirror 34, and also to the galvanometric mirror 22 via a galvanometric mirror control circuit 50 and to the image rotator 21 via the image rotator driving means 21a so as to control their operations. Furthermore, the output of the linear CCD 42 is connected to the galvanometric mirror control circuit 50 via a blood vessel position detection circuit 51.

Figure 4:
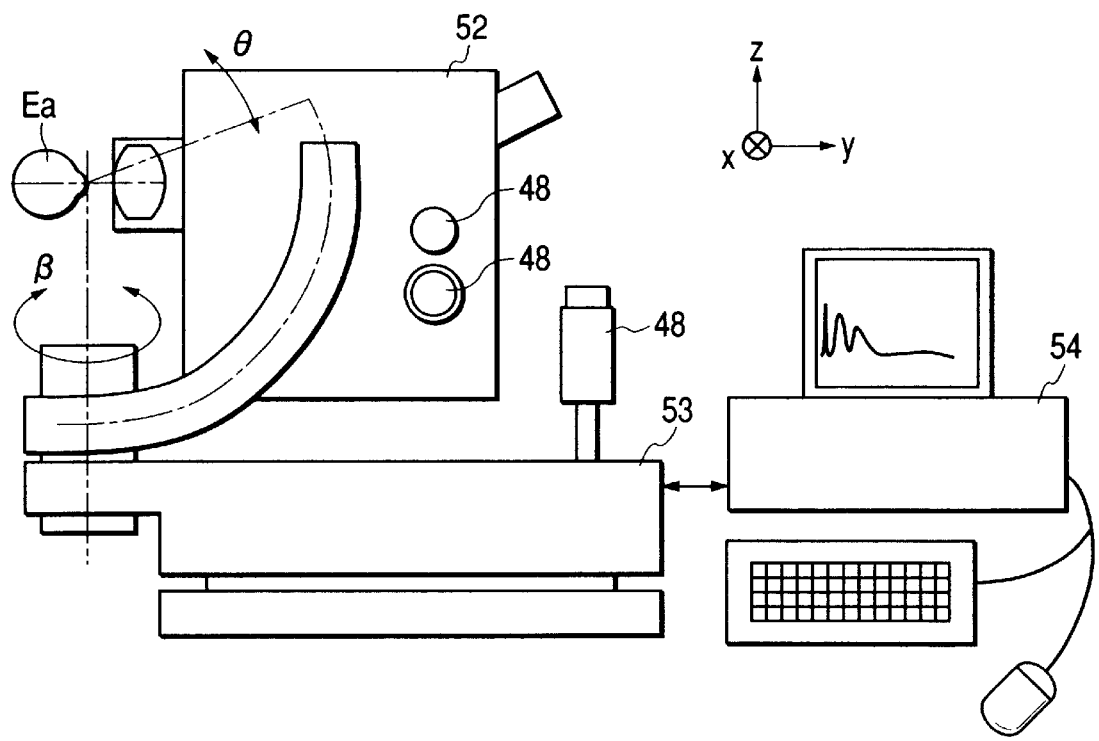
FIG. 4 is a view showing the arrangement of a fundus blood flow measurement apparatus.

FIG. 4 shows the arrangement of a fundus blood flow measurement apparatus. In the fundus hemodromometer, a measurement head 52 that houses members from the observation light source 1 to the photomultipliers 46a and 46b except for the liquid crystal monitor 20 shown in FIG. 1 is placed on a stage 53 that incorporates the system control unit 47 and the like, and is movable in the X-, Y-, and Z-directions. The fundus hemodromometer has an information processing means 54, such as a personal computer or the like, to which the output of the system control unit 47 is connected. The information processing means 54 receives a measurement signal from the system control unit 47, and analyzes, displays, and stores the measurement signal. Conversely, the system control unit 47 controls the apparatus upon receiving processing information from the information processing means 54.

The stage 53 can rotate the position of the objective lens 2 within the range of angle β in the horizontal direction by a panning mechanism and within the range of angle θ in the vertical direction by a tilting mechanism to have the vertex of the cornea of the eye E to be examined as a center. With this mechanism, an arbitrary position on a fundus Ea of the eye E to be examined can be irradiated with a light beam emerging from the objective lens 2. In place of line-of-sight guidance by means of movement of a fixation reference mark, the system control unit 47 may control driving of the panning and tilting mechanisms to move the output measurement light itself on the fundus Ea.

White light emitted by the observation light source 1 passes through the condenser lens 3, and only yellow wavelength light is transmitted through the field lens 4 with a bandpass filter. The yellow wavelength light passes through the ring slit 5, the light-shielding member 6, and the relay lens 7, and illuminates the transmission liquid crystal plate 8 from behind. The light transmitted through the liquid crystal plate 8 passes through the relay lens 9 and light-shielding member 10, and is reflected by the mirror 11 with a hole. Only the wavelength light in the yellow wavelength range is then transmitted through the bandpass mirror 12, passes through the objective lens 2, temporarily forms a fundus illumination light optical image on the pupil Ep of the eye E to be examined, and then nearly uniformly illuminates the fundus Ea.

Figure 2:
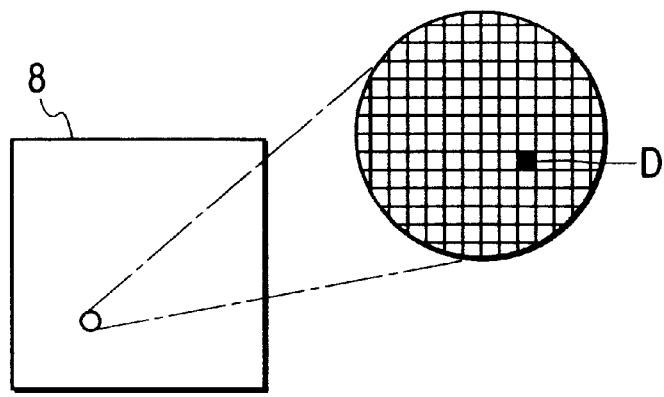
FIG. 2 is an explanatory view of a fixation reference mark on a transmission liquid crystal plate.

At this time, when some elements in the fine matrix of the transmission liquid crystal plate 8 are inverted to dark, as shown in FIG. 2, a dark inverted portion D is projected onto the fundus Ea of the eye E to be examined, and is presented to the eye E to be examined as a fixation reference mark image D'. The system control unit 47 detects if the input means 49 for moving fixation reference mark is operated by the operator, and moves the position of this fixation reference mark image D' in accordance with that operation, thus guiding the fixation position of the eye E to be examined.

Light reflected by the fundus Ea returns along the same optical path, and is output as a fundus observation light beam from the pupil Ep. That light passes through the central aperture of the mirror 11 with a hole, the focusing lens 13, and the relay lens 14, temporarily forms a fundus image Ea' on the scale plate 15, and then reaches the optical path switching mirror 16. When the optical path switching mirror 16 is inserted into the optical path, the fundus image Ea' can be observed by the eye e of the ophthalmic technician via the eyepiece 17; when the optical path switching mirror 16 is retracted from the optical path, the fundus image E"a' formed on the scale plate 15 is formed again of the CCD camera 19 by the TV relay lens 18 and is displayed on the liquid crystal monitor 20. Note that the ophthalmic technician selects an appropriate observation method depending on the purpose, and aligns the apparatus while observing the fundus image Ea' via the eyepiece 17 or liquid crystal monitor 20. Note that the fundus image Ea' on the CCD camera 19 may be sent to the information processing means 54, and may be recorded as image data so as to use the apparatus of this embodiment as a fundus camera.

Measurement light emitted by the measurement light source 36 is collimated by the collimator lens 35. When the optical path switching mirror 34 is inserted into the optical path, the collimated light is reflected by the optical path switching mirror 34 and stationary mirror 33, and passes through a lower portion of the condenser lens 30; when the optical path switching mirror 34 is retracted from the optical path, the collimated light directly passes through an upper portion of the focusing lens 30. The light that has left the lens 30 is transmitted through the dichroic mirror 29. The measurement light then forms a spot image at a position conjugate with the center of the aperture of the mask 31 by the focusing lens 30.

On the other hand, the beam size of tracking light emitted by the tracking light source 38 is expanded at different vertical and horizontal magnifications by the beam expander 37, and the tracking light is then reflected by the mirror 32. After that, the tracking light is shaped into a desired pattern by the shaping mask 31, and is reflected by the dichroic mirror 29 to be superposed on the measurement light.

Furthermore, the measurement light and tracking light pass through the lens 24, are tentatively reflected by the upper reflection surface 22b of the galvanometric mirror 22, pass through the sunspot plate 27, and are then reflected by the concave mirror 28. The measurement light and tracking light return toward the galvanometric mirror 22 via the sunspot plate 27 again and the optical path length compensation meniscus plate 26. In the relay optical system, since the two light beams reflected by the rear side of the galvanometric mirror 22 by inserting/retracting the optical switching mirror 34 into/from the optical path return to the position of the notch portion of the galvanometric mirror 22 due to the function of the relay optical system of the galvanometric mirror 22, they travel toward the image rotator 21 without being reflected by the galvanometric mirror 22. These two light beams pass through the image rotator 21, and are deflected toward the objective lens 2 by the bandpass mirror 12. Then, the two light beams strike the fundus Ea of the eye E to be examined via the objective lens 2, and the tracking light and measurement light are respectively displayed as a rectangular indicator T and spot light U.

Light scattered and reflected by the fundus Ea is focused by the objective lens 2, is reflected by the bandpass mirror 12, and passes through the image rotator 21. Then, the light is reflected by the lower reflection surface 22a of the galvanometric mirror 22, passes through the focusing lens 23, and is split into the measurement light and tracking light by the dichroic mirror 39.

The tracking light is transmitted through the dichroic mirror 39, and forms a blood vessel image Ev' on the linear CCD 42 via the field lens 40 and imaging lens 41 to be larger than the fundus image Ea' formed by the fundus observation optical system. The reflected light of the tracking light with which the fundus Ea is irradiated is projected onto the linear CCD 42 at a magnification of −nx via the image rotator 21 and galvanometric mirror 22. Hence, the reflected light of the tracking light stands still on the linear CCD 42 independently of rotation of the indicator T formed by the tracking light on the fundus Ea by the image rotator 21 or its longitudinal movement on the fundus Ea by the galvanometric mirror 22. When the indicator T moves in the longitudinal direction, the blood vessel image Ev' alone moves on the linear CCD 42, as shown in FIG. 5, and the linear CCD 42 and a blood vessel Ev to be measured intersect in terms of the optical arrangement.

Based on the blood vessel image Ev' sensed by the linear CCD 42, the blood vessel position detection circuit 51 generates data indicating the moving amount of the blood vessel image Ev', and outputs it to the galvanometric mirror control circuit 50. The galvanometric mirror control circuit 50 drives the galvanometric mirror 22 to compensate for this moving amount, thus tracking the blood vessel Ev to be measured.

At this time, since illumination light coming from the observation light source 1 does not reach the linear CCD 42 due to the spectral characteristics of the bandpass mirror 12, the linear CCD 42 senses only the blood vessel image Ev' formed by the tracking light. Also, since hemoglobin in blood and pigment epithelial melanin have quite different spectrum reflectance levels in the green wavelength range, the blood vessel image Ev' can be sensed with high contrast using green light as the tracking light.

Figure 5:
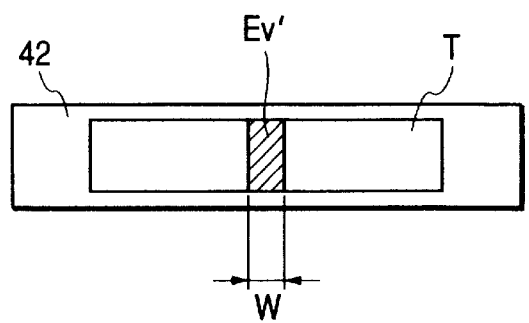
FIG. 5 is an explanatory view of a blood vessel image on a linear CCD.
Figure 6:
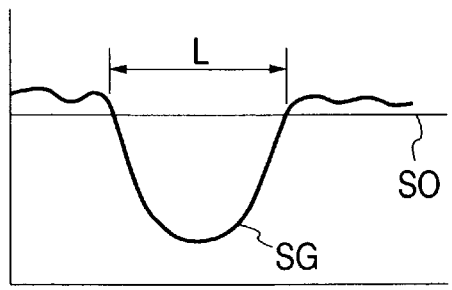
FIG. 6 is a graph of blood vessel diameter information.

As shown in the liquid crystal monitor 20 in FIG. 1, when a portion of the indicator T is superimposed on the blood vessel Ev to be measured, the blood vessel image Ev' indicated and illuminated by the indicator T is enlarged, as shown in FIG. 5, and is projected onto the linear CCD 42 of the blood vessel detection system to have a width W. At this time, the output signal from the linear CCD 42 is as shown in, e.g., FIG. 6, and the blood vessel position detection circuit 51 obtains a length corresponding value L by comparing an output signal SG from the linear CCD 42 with a reference signal SO, thus computing an intersection width W between the linear CCD 42 and blood vessel image Ev'. Also, in the blood vessel position detection circuit 51, the galvanometric mirror control circuit 50 drives the galvanometric mirror 22 on the basis of the output from the linear CCD 42 to make tracking control, which locates the central position of the intersection width W on the reference position of the linear CCD 42, so that the blood vessel Ev to be measured and linear CCD 42 always intersect at an appropriate position.

The information of the intersection width W of the intersection detected by the blood vessel position detection circuit 51 is sent to the system control unit 47. The system control unit 47 drives the driving means 21a to pivot the image rotator 21 and makes the following control. That is, the system control unit 47 compares intersection widths W detected during rotation of the indicator T, and stops the image rotator 21 at an angle that yields a minimum intersection width W. At this time, the indicator T is perpendicular to the running direction of the blood vessel Ev to be measured, and the intersection width W computed from its length corresponding value L is used as blood vessel diameter information d of the blood vessel Ev to be measured.

The system control unit 47 detects the rotation angle of the image rotator 21 from control information of the driving means 22a, and specifies the running direction of the blood vessel Ev to be measured at a position irradiated with the tracking light. When the system control unit 47 automatically controls the rotation angle of the image rotator 21 to always minimize the intersection width W by the driving means 21a, even when the irradiation position moves on the blood vessel Ev, the direction the blood vessel Ev to be measured runs can always be detected.

On the other hand, the measurement light is reflected by the dichroic mirror 39, and is reflected by the pair of mirrors 45a and 45b via an aperture of the confocal stop 44. The light beams reflected by the mirrors 45a and 45b are respectively received by the photomultipliers 46a and 46b. Light-receiving signals from the photomultipliers 46a and 46b are sent to the information processing means 54 via the system control unit 47, and undergo frequency analysis to obtain blood flow velocity information v of the fundus Ea. That result is saved in the information processing means 54 together with the blood vessel shape information d, and is displayed together.

Upon measurement, the ophthalmic technician operates the operation input means 48 to align the apparatus to the eye E to be examined, and to adjust focus on the blood vessel Ev to be measured. Then, the ophthalmic technician operates the input means 49 for moving the fixation reference mark to guide the line of sight of the eye E to be examined, and superimposes the indicator T on the blood vessel Ev to be measured. In this case, when the ophthalmic technician operates the operation input means 48 to irradiate the blood vessel Ev to be measured with measurement light, the blood flow velocity information v is processed in a state that the ophthalmic technician can discriminate, and is presented by the information processing means 54. The ophthalmic technician discriminates the blood flow velocity information v, and guides the line of sight using the input means 49 for moving the fixation reference mark so as to change the measurement position to a position where the best blood flow velocity information v can be obtained. Finally, the ophthalmic technician discriminates and actually measures the blood flow velocity information v.

Figure 7A:
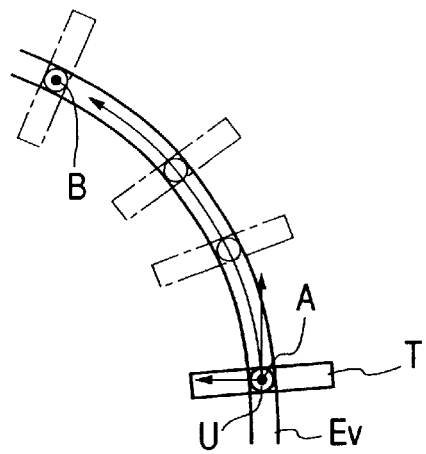
FIGS. 7A and 7B are explanatory views of measurement light on a blood vessel.

Upon operation of the input means 49 for moving the fixation reference mark, the system control unit 47 drives the transmission liquid crystal plate 8 to move the dark inverted portion D of the fine matrix. At this time, when the ophthalmic technician moves input means 49 for moving the fixation reference mark from the side in front of the plane of the paper toward that paper, the fixation reference mark image D' moves in the up-and-down direction; when he or she moves the means 49 in the right-and-left direction, the image D' moves in the right-and-left direction. For example, as for a curved blood vessel, as shown in FIG. 7A, the movement of the fixation reference mark image D' is controlled based on the input signal at the input means 49 for moving the fixation reference mark and a detection signal from a blood vessel direction detection circuit to guide the fixation position of the eye E to be examined, so that the irradiation position of the measurement light scans from A to B on the blood vessel Ev. Hence, the ophthalmic technician can simply move the input means 49 in the left or up direction (in the case of scanning from B to A, the right or down direction).

Figure 7B:
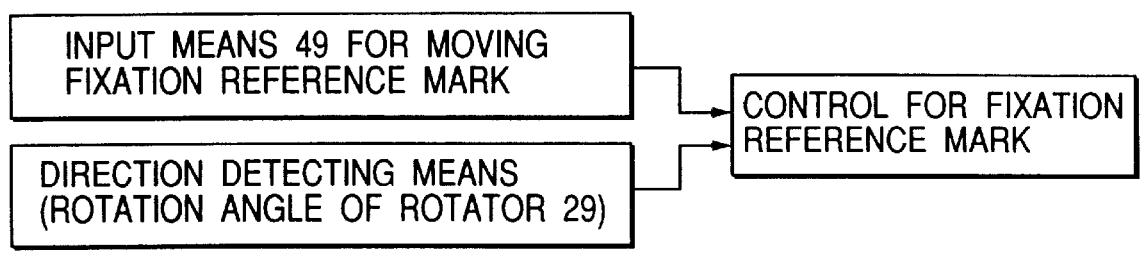

In this manner, as shown in FIG. 7B, the system control unit 47 compares the operation direction of the input means 49 for moving the fixation reference mark and the blood vessel running direction, while always detecting the direction in which the blood vessel runs, and determines the direction closest to that operation direction to be the moving direction of the measurement light. The system control unit 47 drives the transmission liquid crystal plate 8 to move the dark inverted portion D so that the direction in which the blood vessel runs agrees with the determined direction. In this manner, the fixation reference mark image D' moves along the direction on the fundus Ea in which the blood vessel runs to guide the eye E to be examined, and the measurement light consequently scans on the blood vessel Ev. Using blood vessel tracking to absorb any position error of the fixation reference mark image D' and any deviation of the eye E to be examined from the direction in which the blood vessel runs, the measurement light can accurately move on the blood vessel Ev.

This process is repeated until the operation of the input means 49 for moving fixation the reference mark is canceled. The ophthalmic technician checks the blood flow velocity information v obtained by the information processing means 54, and stops the movement of the measurement light at a position where satisfactory measurement can be done, thus making actual measurement.

On the other hand, the reliability of the blood flow velocity information v evaluated by the ophthalmic technician can be automatically evaluated by adopting the following processing algorithm.

Figure 8:
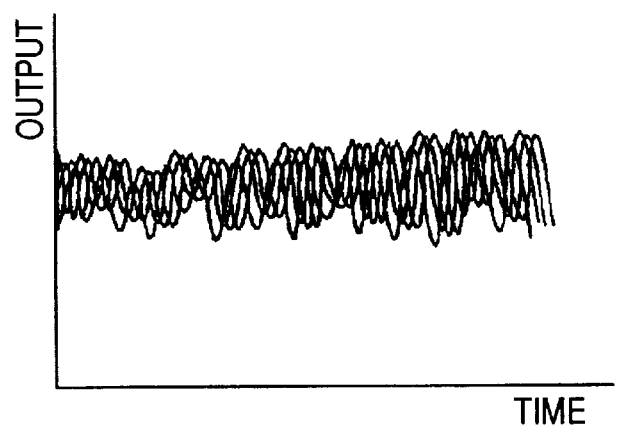
FIG. 8 is a graph of a Doppler shift measurement signal.
Figure 9:
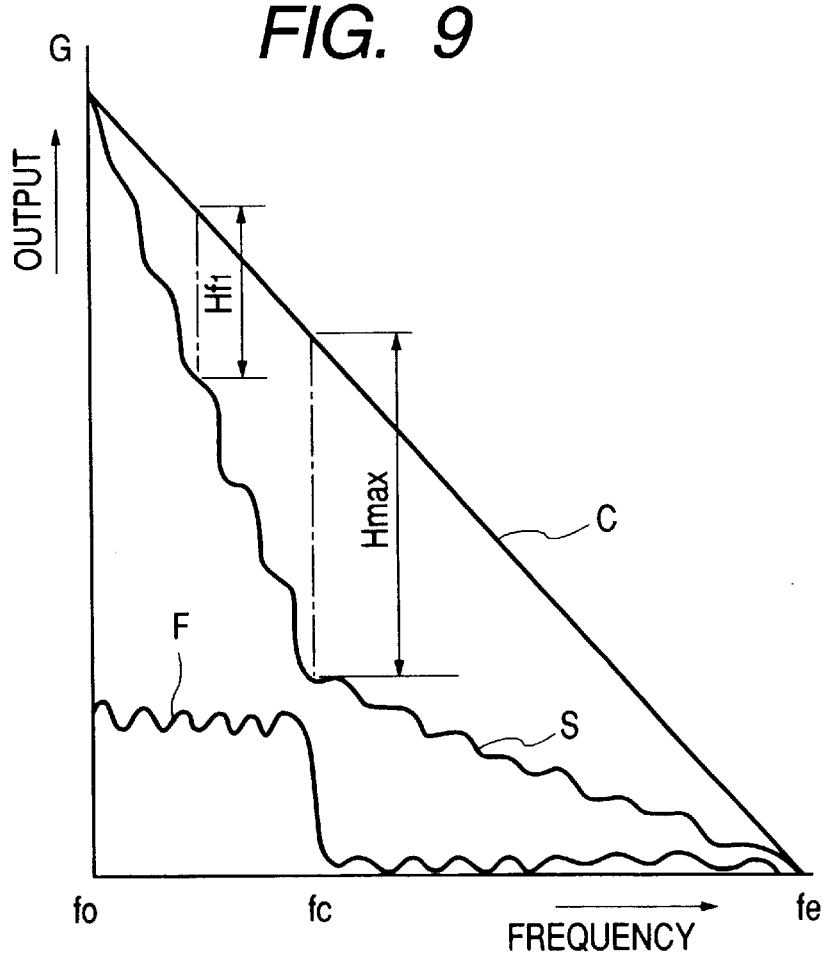
FIG. 9 is a graph showing an FFT analysis curve and integral curve of the Doppler shift measurement signal.

FIG. 8 shows a primary signal of a blood flow state obtained from the laser Doppler shift. The ordinate plots the output, and the abscissa time. When this signal undergoes frequency analysis by Fast Fourier transform (FFT), an FFT transform curve F shown in FIG. 9 is obtained. In FIG. 9, the ordinate plots the output, and the abscissa plots the frequency indicating velocity. In the left portion of the transform curve F, a frequency corresponding to an abrupt output drop from a frequency range of a roughly constant output is present, and is called a cutoff frequency fc, which corresponds to the highest velocity of an objective region measured by the laser Doppler shift. The cutoff frequency fc is computed by the information processing means 54 by analyzing the transform curve F.

Furthermore, FIG. 9 shows an FFT integral curve S obtained by integrating the transform curve F within the range from sampling frequencies fc to fo, and a second ground line C that connects a point G where the integral curve S intersects with a frequency fo and a frequency fe. Hfi (fi=fo to fe) represents the vertical distance from the second ground line C to the integral line S at each appropriate point between frequencies fo and fe, and Hmax is the maximum value of Hfi.

Figure 10:
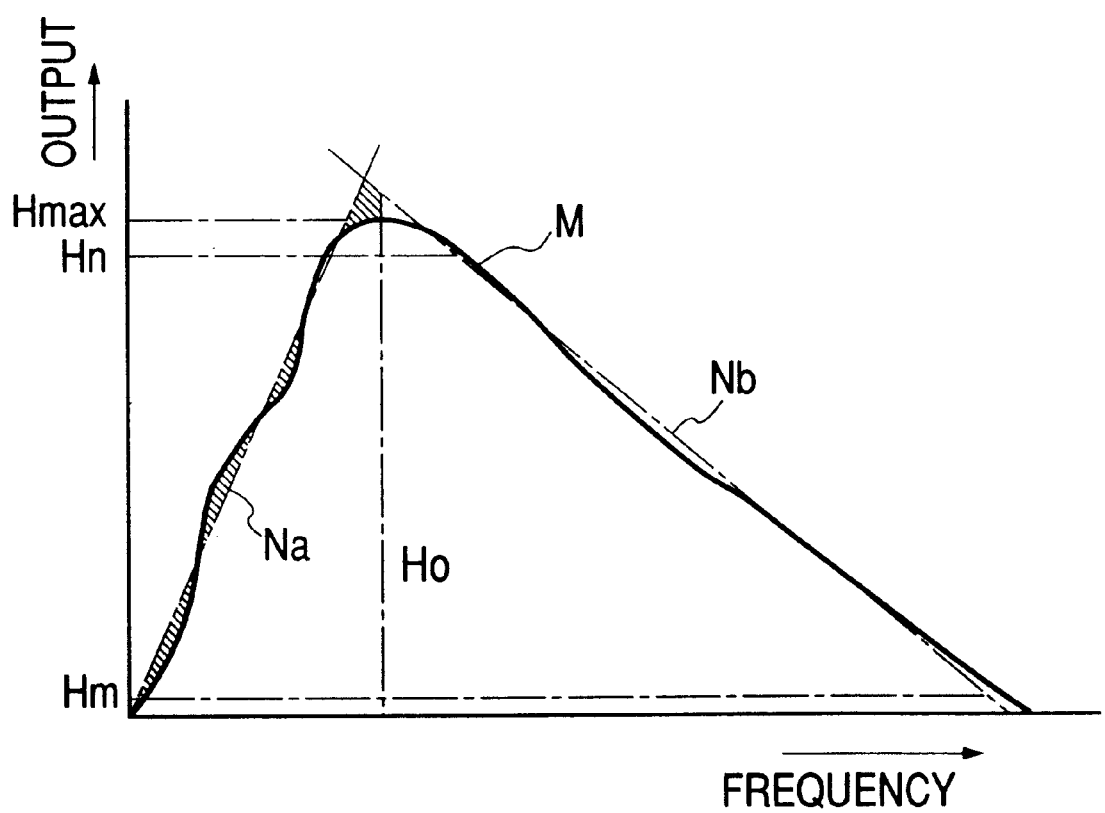
FIG. 10 is a graph of reliability evaluation by analyzing the integral curve.

FIG. 10 shows an Hfi curve M, in which the ordinate plots the Hfi output and the abscissa plots the frequency. Let Hm be an m % value of the maximum value Hmax. and Hn be its n % value. When an Hm–Hn section of the Hfi curve M is linearly approximated using the method of least squares, lines Na and Nb are obtained. Let Ho be a perpendicular dropped from the maximum value Hmax of the Hfi curve M. Then, the total area of regions bounded by the Hfi curve M and line Na, and by the Hfi curve M, line Na, and perpendicular Ho is computed to obtain a quality value Q. As the quality value Q becomes smaller, it indicates that the Hfi curve M is more approximate to a line, i.e., the integral curve S is more approximate to a line. This means that variations of the transform curve F are small, implying a good measurement state. Note that values 0 to Qn of the quality value Q within the range in which satisfactory blood flow velocity information v is obtained are set in advance.

In this manner, the blood vessel Ev to be measured is irradiated with measurement light by operating the operation input means 48, the system control unit 47 is switched to a trace mode, and the input means 49 for moving the fixation reference mark is operated to move measurement light in a desired direction. The system control unit 47 drives the transmission liquid crystal plate 8 to guide the line of sight of the eye E to be examined along the blood vessel Ev while executing the same processes as above, thus tracing the measurement light on the blood vessel Ev. During this control, the system control unit 47 always discriminates if the quality value Q received from the information processing means 54 falls within the range from O to Qn. If this discrimination is made every time the irradiation position moves, the quality of a measurement signal at the irradiation position after the movement can always be evaluated. The information processing means 54 always monitors the quality value Q. When the quality value Q falls within the range from O to Qn, the means 54 outputs a stop signal to the system control unit 47. In response to this signal, the system control unit 47 stops driving the transmission liquid crystal plate 8, and is ready to measure.

If measurement is made by seeking a measurement point that minimizes the quality value Q during scanning, it can be made with an optimal measurement signal. The system control unit 47 drives the transmission liquid crystal plate 8 to scan the measurement light on the blood vessel Ev, and the information processing means 54 stores a quality value Q at each measurement point and the position of the measurement point every time the fixation reference mark image D' moves. After scanning has been done within the pre-set range, the system control unit 47 compares quality values stored at the respective points and drives the transmission liquid crystal plate 8 to move the measurement light to the measurement point where the minimum value was obtained, thus moving the fixation reference mark image D' and setting a ready-to-measure state.

In order to find out an optimal measurement position more easily, the system control unit 47 drives the transmission liquid crystal plate 8 to automatically scan the measurement light on the blood vessel Ev from the blood vessel scan start point in two directions in the trace mode, and finds a point that can produce a minimum quality value Q during scanning to allow measurement, in place of making the ophthalmic technician designate the direction to scan.

In order to allow the ophthalmic technician to select a portion to be measured more accurately, the positions and quality values Q at a plurality of points at which the quality value Q falls within the range from 0 to Qn are displayed together, and the system control unit 47 can drive the transmission liquid crystal plate 8 to move the measurement light to an arbitrary point selected by the ophthalmic technician, in place of returning to a point that produces a minimum quality value Q obtained during scanning.

When a satisfactory quality value Q cannot be obtained, the scan start position is stored to easily restart a search for the portion to be measured, and the system control unit 47 can drive the transmission liquid crystal plate 8 so that the measurement light returns to the scan start position irrespective of the current position during blood vessel scanning upon operation of the operation input means 48.

While the system control unit 47 is scanning the blood vessel, a patient may blink or move his or her eye largely, and the continuity of scanning points may be disrupted or the measurement light may deviate from the portion to be measured way too much. To cope with this situation, a blink detection mechanism or eyeball motion detection means (not shown) detects the blinking or large line-of-sight movement of the patient, and the system control unit 47 stops scanning of the blood vessel. In order to protect the eye to be examined, when a predetermined time set by the operation input means 48 or the like has elapsed, the system control unit 47 stops scanning of the blood vessel.

Furthermore, when the measurement conditions are to be changed as needed while moving the portion to be measured, for example, if the input means 49 for moving the fixation reference mark is operated in the direction to move and returns to a position near the center within a predetermined period of time, the fixation reference mark image D' may stop with a minimum moving amount, or if the input means 49 for moving the fixation reference mark is continuously operated in the direction to move for a predetermined period of time or more, blood vessel scanning may be automatically started in the direction to be operated.

In this manner, since a portion where a high-quality Doppler shift measurement signal can be obtained can be accurately and easily determined, and measurement light is automatically moved in cooperation with the determination result of the measurement signal, and the fundus blood flow velocity can be accurately and quickly measured irrespective of the skill of the ophthalmic technician. Also, when a plurality of sets of quality values of measurement signals and measurement positions are stored and displayed, the position to be measured can be accurately selected, and a measurement position that can produce the best quality value can be easily found. Hence, measurement can be done with the best measurement signal.

Since the measurement light is easily returned to the scan start position, a measurement point search can be easily repeated, and a position with good measurement conditions can be accurately found. On the other hand, when the measurement light deviates from the position to be measured, since scanning is stopped, a measurement point search with continuity and high reliability can be made. Furthermore, since scanning is stopped after the elapse of a predetermined period of time, the eye E under examination can be protected, and the measurement point can be moved intermittently or sequentially. Hence, a measurement point search with higher accuracy can be made while setting measurement conditions most suitable for the measurement point at a destination.

To restart, since a fundus blood vessel examination apparatus according to the present invention can move the position irradiated with measurement light along the direction in which the fundus blood vessel runs on the basis of information indicating this direction, the measurement light can accurately and easily move on the blood vessel to be measured. Therefore, a high-quality Doppler shift measurement signal can always be obtained irrespective of variations of the quality of the Doppler shift measurement signal from the fundus blood vessel due to indefinite factors of the living body.

What is claimed is:

1. Fundus blood vessel examination apparatus comprising:
    an irradiation optical system for irradiating a fundus blood vessel with measurement light;
    light-receiving means for receiving scattered light of the measurement light from the fundus blood vessel;
    measurement means for detecting predetermined information from the fundus blood vessel on the basis of information from said light-receiving means;
    direction detection means for detecting a direction in which a bloodstream flows in the fundus blood vessel;
    irradiation position changing means for changing the irradiation position of the measurement light on the fundus blood vessel driven by drive means; and
    control means for controlling said irradiation position changing means to adjust the irradiation position of the measurement light on the fundus blood vessel by the drive means on the basis of the running direction information detected by said direction detection means to move the irradiation position of the measurement light along the direction in which the fundus blood vessel runs.

2. An apparatus according to claim 1, further comprising means for determining the direction in which the fundus blood vessel runs and for determining a moving direction after the irradiation position of the measurement light is moved.

3. An apparatus according to claim 1, wherein said measurement means comprises evaluation means for evaluating the reliability of the predetermined information, and said evaluation means evaluates the reliability of the predetermined information as needed after the irradiation position of the measurement light is moved.

4. An apparatus according to claim 3, wherein said control means changes the irradiation position of the measurement light on the basis of an evaluation result of said evaluation means, and moves the the irradiation position of the measurement light to a nearby position where the predetermined information has a predetermined reliability.

5. An apparatus according to claim 4, further comprising storage or display means for storing or displaying a moved irradiation position of the measurement light and data representing the reliability corresponding to the moved position every time the irradiation position of the measurement light is moved.

6. An apparatus according to claim 5, further comprising:
    moving range setting means for setting a predetermined moving range; and
    automatic scanning means for automatically moving the irradiation position of the measurement light within the moving range.

7. An apparatus according to claim 4, further comprising:
    storage means for storing a movement start position of the irradiation position of the measurement light; and
    irradiation position return means for returning the irradiation position of the measurement light to the movement start position irrespective of the irradiation position of the measurement light during movement.

8. An apparatus according to claim 1, further comprising:
    presentation means for presenting a fixation reference mark to an eye to be examined, and
    wherein said control means controls the position of the fixation reference mark presented by said presentation means.

9. A fundus blood vessel measurement apparatus comprising:
    presentation means for presenting a fixation reference mark to an eye to be examined;
    irradiation means for irradiating a blood vessel on a fundus of an eye with measurement light in accordance with the position of the fixation reference mark;
    light-receiving means for receiving reflected light of the measurement light by the fundus;
    computation means for computing blood vessel information of a fundus blood vessel on the basis of a light-received output of said light-receiving means;

direction detection means for detecting a longitudinal direction of the blood vessel; and position control means for controlling the position of the fixation reference mark in accordance with the direction detected by said direction detection means.

10. An apparatus according to claim 9, further comprising:

an input member for changing the position of the fixation reference mark, and wherein said position control means controls the position of the fixation reference mark on the basis of a direction detection signal from said direction detection means and an input signal of said input member.

11. An apparatus according to claim 9, wherein said direction detection means comprises an image sensing element for sensing a blood vessel image.

12. An apparatus according to claim 11, wherein said image sensing element comprises an array type sensor.

13. An apparatus according to claim 11, wherein said direction detection means further comprises an image rotator, which is inserted between said image sensing element and the eye to be examined, and which is adapted to rotate the blood vessel image with respect to said image sensing element.

14. An apparatus according to claim 13, wherein said image rotator is rotated in accordance with an output from said image sensing element.

15. An apparatus according to claim 13, wherein said image rotator is rotated in accordance with an output from said image sensing element to locate the blood vessel image in a predetermined direction.

16. An apparatus according to claim 15, wherein the direction detected by said direction detection means is a rotation angle of said image rotator.

17. An apparatus according to claim 9, wherein said position control means controls the position of the fixation reference mark to irradiate the blood vessel with the measurement light along a longitudinal direction thereof.

* * * * *

UNITED STATES PATENT AND TRADEMARK OFFICE
CERTIFICATE OF CORRECTION

PATENT NO.    : 6,411,839 B1
DATED         : June 25, 2002
INVENTOR(S)   : Satoru Okinishi It is certified that error appears in the above-identified patent and that said Letters Patent is hereby corrected as shown below:

<u>Title page,</u>
Item [57], ABSTRACT,
Line 7, "fundus" should read -- fundus. --.

<u>Column 1,</u>
Line 41, "eve" should read -- eye --.

Signed and Sealed this

Twenty-fifth Day of February, 2003

JAMES E. ROGAN
*Director of the United States Patent and Trademark Office*